US00PP09746P

United States Patent [19]

Dümmen

[11] Patent Number: Plant 9,746

[45] Date of Patent: Dec. 10, 1996

[54] GERANIUM PLANT NAMED 'HWD JUBILA'

[75] Inventor: Günter Dümmen, Rheinberg-Eversael, Germany

[73] Assignee: Dummen Jungpflanzenkulturen, Rheinberg-Eversael, Germany

[21] Appl. No.: 520,863

[22] Filed: Aug. 30, 1995

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Proprietary Rights International

[57] ABSTRACT

A new and distinct cultivar of geranium plant named HWD Jubila, characterized by its semi-double lilac pink flowers; reddish brown peduncles and pedicels; dark green foliage; and freely branching plant habit.

1 Drawing Sheet

The present invention relates to a new and distinct cultivar of geranium plant, botanically known as *Pelargonium×hortorum,* known as the variety Duejub, and hereinafter referred to by the cultivar name HWD Jubila.

The new cultivar is a product of a planned breeding program conducted by the inventor in Rheinberg, Germany. The objective of the breeding program was to develop a new semi-double geranium with pink flowers and dark-green foliage.

The new cultivar originated from a cross made by the inventor of the patented cultivar Fisrix (U.S. Plant Pat. No. 7,422) as the male or pollen parent with the proprietary selection 86-8-5 as the female or seed parent.

The cultivar HWD Jubila was discovered and selected by the inventor as a flowering plant within the progeny of the stated cross in a controlled environment in Rheinberg, Germany. Asexual reproduction of the new cultivar by terminal cuttings taken at Rheinberg, Germany, has shown that the unique features of this new geranium are stabilized and reproduced true to type in successive generations of asexual reproduction.

The following traits have been repeatedly observed and are determined to be the unique characteristics of HWD Jubila. These characteristics in combination distinguish HWD Jubila as a new and distinct cultivar:

1. Semi-double lilac pink flowers.
2. Reddish brown peduncles and pedicels.
3. Dark green foliage.
4. Freely branching plant habit.

In comparison to the parent cultivar Fisrix, plants of the new geranium have semi-double (not single) flowers, shorter peduncles, larger flowers, no red marks on the petals, and darker pink flower color. In comparison to the parent selection 86-8-5, plants of the new geranium flower later, have smaller flowers, and darker green foliage color.

The accompanying colored photograph illustrates the overall appearance of the new cultivar, showing the colors as true as it is reasonably possible to obtain in colored reproductions of this type. The photograph comprises a top perspective view of a typical potted plant of HWD Jubila with one plant in a 10-cm container.

The cultivar HWD Jubila has not been observed under all possible environmental conditions. The phenotype may vary somewhat with variations in environmental such as temperature and light intensity, without, however, any variance in genotype. The following observations, measurements and comparisons describe plants grown in Rheinberg, Germany, under commercial practice in a glass-covered greenhouse with day temperatures of 24° C. and night temperatures of 18° to 20° C. and light levels of 45,000 to 60,000 lux. Plants were grown in 10-cm pots with one plant per pot.

In the following description, color references are made to The Royal Horticultural Society Colour Chart except where general terms of ordinary dictionary significance are used.

Classification:

*Botanical.*—*Pelargonium×hortorum.*

*Commercial.*—Zonal geranium.

*Cultivar.*—'HWD Jubila'.

Parentage:

*Male parent.*—Patented cultivar Fisrix (U.S. Plant Pat. No. 7,422).

*Female parent.*—Proprietary selection 86-8-5.

Propagation:

*Type cutting.*—Terminal cuttings.

*Time to initiate roots.*—Summer: 27° C., 21 days; winter: 20° C., 28 days.

Plant Description

General appearance: Rounded; compact plant size; upright; freely branching.

Foliage description:

*Arrangement.*—Generally alternate.

*Shape.*—Orbicular with rounded tip and cordate base.

*Size.*—Length: 6 to 7 cm. Width: 8 cm.

*Texture.*—Velvety; pubescent on upper and under surfaces.

*Margin.*—Crenate.

*Color.*—Young foliage, upper surface: 147A. Young foliage, under surface: 147B. Mature foliage, upper surface: 147A. Mature foliage, under surface: 147B. Zonation pattern: None. Veins, upper surface: 144B. Veins, under surface: 144B. Petiole: Greener than 146B.

*Venation pattern.*—Palmate.

*Petiole.*—Length: 7 to 9 cm. Diameter: 2 to 3 mm.

Stem description:

*Internode length.*—0.5 to 1 cm.

*Stem color.*—144A.

*Lateral branch number.*—15 to 18.

*Lateral branch length.*—7 to 10 cm.

Flowering Description

Flowering habit: Freely flowering. Flowers arranged in umbels.

Natural flowering season: Year-round.

Flowers borne: Flower buds develop in apical leaf axils. Umbels are displayed above the foliage.

Quantity of inflorescences: Very floriferous; usually 8 to 10 open umbels and at least 3 developing umbels per plant at one time.

Umbels:
- *Form.*—Rounded.
- *Diameter.*—10 to 12 cm.
- *Depth (height).*—5 cm.

Flowers:
- *Form.*—Semi-double.
- *Shape.*—Rounded.
- *Quantity of flowers per umbel.*—18 to 20.
- *Diameter.*—4 to 5 cm.
- *Depth (height).*—1.5 cm.

Petals:
- *Shape.*—Obovate with rounded tip.
- *Arrangement.*—Rosette, overlapping.
- *Quantity.*—6.
- *Aspect.*—Flat.
- *Size.*—Length: 2.8 cm. Width: 2.5 cm.
- *Texture.*—Satiny, smooth.
- *Margin.*—Entire.
- *Color.*—When opening, upper surface: 67C/67D. When opening, under surface: 68B at margin, fading to 56D at pedicel, venous areas, 58B. Upper surface: 67C/67D, venous areas, 66A. Under surface: 68B at margin, fading to 56D at pedicel, venous areas, 58B.

Petaloids:
- *Shape.*—Irregular, generally obovate with rounded or clefted tip.
- *Arrangement.*—Rosette, overlapping.
- *Quantity.*—4 to 7.
- *Size.*—Length: 1 to 2.5 cm. Width: 0.5 to 1.5 cm.
- *Texture.*—Satiny, smooth.
- *Margin.*—Generally entire.
- *Color.*—When opening, upper surface: 67C/67D. When opening, under surface: 68B at margin, fading to 56D at pedicel, venous areas, 58B. Upper surface: 67C/67D, venous areas, 66A. Under surface: 68B at margin, fading to 56D at pedicel, venous areas, 58B.

Peduncle (umbel stem):
- *Angle.*—Erect.
- *Length.*—10 to 12.5 cm.
- *Pubescence.*—Very fine.
- *Color.*—144A at base, generally 183A with greenish tint.

Pedicel (individual flower stem):
- *Angle.*—Erect, rigid.
- *Length.*—3.5 to 3.8 cm.
- *Pubescence.*—Very fine.
- *Color.*—183C.

Flower bud:
- *Shape.*—Ovoid.
- *Length.*—1.5 cm.
- *Diameter.*—9 mm.
- *Color.*—55B, 61B on edge.

Sepals:
- *Arrangement.*—Rosette.
- *Quantity.*—5 to 6.
- *Size.*—Length: 1.2 cm. Width: 4 to 5 mm.
- *Shape.*—Acuminate with apiculate tip.
- *Texture.*—Velvety.
- *Margin.*—Entire.
- *Color.*—Upper surface: 183C at base fading to 144A at tip. Under surface: 183B at base fading to 144A at tip.

Reproductive organs:
- *Androecium.*—Stamen number: 10 to 12. Anther size: 2 mm. Anther color: 47B. Pollen color: 34C.
- *Gynoecium.*—Pistil number: 1. Pistil lenght: 4 mm. Stigma shape: Decurrent. Stigma color: 46C. Style length: 4 mm. Style color: 46C.

Ploidy level: Tetraploid.

Disease resistance: No fungal, bacterial nor viral problems observed.

Seed development: Seed production is very rarely observed.

It is claimed:

1. A new and distinct cultivar of geranium plant named HWD Jubila, as illustrated and described.

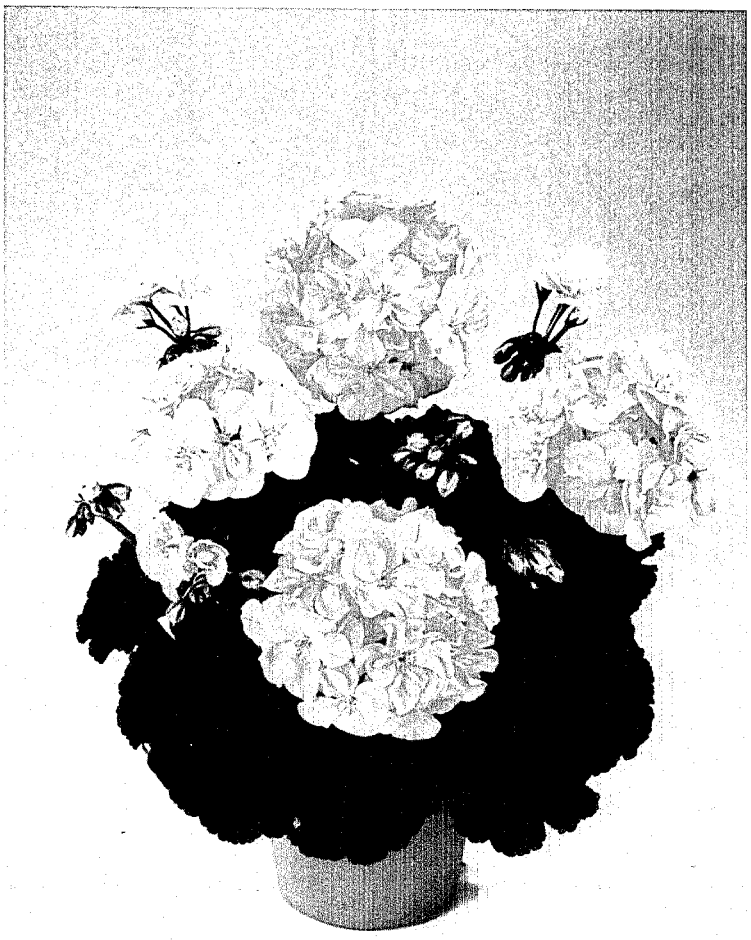

* * * * *